(12) United States Patent
Splinter

(10) Patent No.: US 11,166,647 B2
(45) Date of Patent: Nov. 9, 2021

(54) INTRA-VASCULAR DEVICE WITH PRESSURE DETECTION CAPABILITIES USING PRESSURE SENSITIVE MATERIAL

(71) Applicant: The Spectranetics Corporation, Colorado Springs, CO (US)

(72) Inventor: Robert Splinter, Concord, NC (US)

(73) Assignee: The Spectranetics Corporation, Colorado Springs, CO (US)

( * ) Notice: Subject to any disclaimer, the term of this patent is extended or adjusted under 35 U.S.C. 154(b) by 0 days.

(21) Appl. No.: 15/064,265

(22) Filed: Mar. 8, 2016

(65) Prior Publication Data

US 2016/0183844 A1    Jun. 30, 2016

Related U.S. Application Data

(62) Division of application No. 14/714,925, filed on May 18, 2015, now Pat. No. 9,289,173, which is a division
(Continued)

(51) Int. Cl.
*A61B 5/107* (2006.01)
*A61B 18/24* (2006.01)
(Continued)

(52) U.S. Cl.
CPC .......... *A61B 5/1079* (2013.01); *A61B 5/0084* (2013.01); *A61B 5/1076* (2013.01);
(Continued)

(58) Field of Classification Search
CPC ..... A61B 18/20; A61B 5/0084; A61B 5/1079; A61B 5/107; A61B 5/1076; A61F 9/008
(Continued)

(56) References Cited

U.S. PATENT DOCUMENTS 2,079,117 A    5/1937   Hays
2,238,120 A    4/1941   Launder
(Continued)

FOREIGN PATENT DOCUMENTS

DE    202006020126 U1    12/2007
WO        1998035104 A1     8/1998
WO      WO2000069569 A1    11/2000

OTHER PUBLICATIONS

Aquafog Turbo RSM, copyright 1997, Jaybird Manufacturing, Inc., downloaded from http://web.archive.org/web/19990421053744/ http://www.jaybird-mfg.com/rsm.html on Sep. 18, 2014, 2 pages.
(Continued)

*Primary Examiner* — Jon Eric C Morales

(57) ABSTRACT

A laser catheter with a pressure sensor is provided according to embodiments of the invention. The pressure sensor may be coupled with the distal end of the laser catheter and may comprise any of various piezoelectric materials, for example Polyvinylidene Difluoride (PVDF). In various embodiments of the invention the pressure sensor is configured to detect pressure longitudinally and coaxially. The pressure sensor may provide an electric potential that is proportional to the vessel pressure and may be used to monitor and/or adjust laser parameters. In other embodiments the results from the pressure sensor may be used to determine the vessel size and/or the type of material being ablated.

15 Claims, 9 Drawing Sheets

Related U.S. Application Data of application No. 11/937,583, filed on Nov. 9, 2007, now Pat. No. 9,066,742.

(51) Int. Cl.
*A61B 5/00* (2006.01)
*A61B 90/00* (2016.01)
*A61B 18/00* (2006.01)

(52) U.S. Cl.
CPC ............ *A61B 5/4836* (2013.01); *A61B 18/24* (2013.01); *A61B 18/245* (2013.01); *A61B 2018/00642* (2013.01); *A61B 2018/00732* (2013.01); *A61B 2018/00904* (2013.01); *A61B 2090/065* (2016.02); *A61B 2090/0813* (2016.02); *A61B 2562/0247* (2013.01)

(58) Field of Classification Search
USPC .................................................. 606/13, 15
See application file for complete search history.

(56) References Cited

U.S. PATENT DOCUMENTS

| | | |
|---|---|---|
| 2,551,789 A | 5/1951 | Copley |
| 2,571,069 A | 10/1951 | Shearman |
| 2,576,976 A | 12/1951 | Stagner |
| 2,608,792 A | 9/1952 | Chater |
| 2,635,920 A | 4/1953 | Boyce |
| 2,973,121 A | 2/1961 | Banker |
| 3,446,424 A | 5/1969 | Wolford |
| 4,004,732 A | 1/1977 | Hanson |
| 4,053,845 A | 10/1977 | Gould |
| 4,223,836 A | 9/1980 | Eager |
| 4,564,011 A | 1/1986 | Goldman |
| 4,593,854 A | 6/1986 | Albertsson |
| 4,597,524 A | 7/1986 | Albertsson |
| 4,641,912 A | 2/1987 | Goldenberg |
| 4,657,712 A | 4/1987 | Milbocker |
| 4,686,979 A | 8/1987 | Gruen et al. |
| 4,732,448 A | 3/1988 | Goldenberg |
| 4,747,405 A | 5/1988 | Leckrone |
| 4,784,132 A | 11/1988 | Fox et al. |
| 4,799,754 A | 1/1989 | Goldenberg |
| 4,807,620 A | 2/1989 | Strul et al. |
| 4,809,710 A | 3/1989 | Williamson |
| 4,830,460 A | 5/1989 | Goldenberg |
| 4,844,062 A | 7/1989 | Wells |
| 4,848,336 A | 7/1989 | Fox et al. |
| 4,860,742 A | 8/1989 | Park et al. |
| 4,924,863 A | 5/1990 | Sterzer |
| 4,960,411 A | 10/1990 | Buchbinder |
| 5,016,964 A | 5/1991 | Donnelly |
| 5,041,108 A | 8/1991 | Fox et al. |
| 5,070,882 A | 12/1991 | Bui et al. |
| 5,097,841 A | 3/1992 | Moriuchi et al. |
| 5,112,328 A | 5/1992 | Taboada et al. |
| 5,158,560 A | 10/1992 | Sogawa et al. |
| 5,178,153 A | 1/1993 | Einzig |
| 5,188,632 A | 2/1993 | Goldenberg |
| 5,240,004 A | 8/1993 | Walinsky et al. |
| 5,246,437 A | 9/1993 | Abela |
| 5,250,045 A | 10/1993 | Bohley |
| 5,254,112 A * | 10/1993 | Sinofsky ............ A61B 5/02007 600/439 |
| 5,263,953 A | 11/1993 | Bagby |
| 5,267,341 A | 11/1993 | Shearin |
| 5,299,737 A | 4/1994 | McGinnis et al. |
| 5,304,171 A | 4/1994 | Gregory et al. |
| 5,350,375 A | 9/1994 | Deckelbaum et al. |
| 5,352,197 A | 10/1994 | Hammersmark et al. |
| 5,415,653 A | 5/1995 | Wardle et al. |
| 5,429,604 A | 7/1995 | Hammersmark et al. |
| 5,429,617 A | 7/1995 | Hammersmark et al. |
| 5,440,664 A | 8/1995 | Harrington et al. |
| 5,447,663 A | 9/1995 | Dix et al. |
| 5,456,680 A | 10/1995 | Taylor et al. |
| 5,468,239 A | 11/1995 | Tanner et al. |
| 5,470,330 A | 11/1995 | Goldenberg et al. |
| 5,484,433 A | 1/1996 | Taylor et al. |
| 5,514,128 A | 5/1996 | Hillsman et al. |
| 5,537,499 A | 7/1996 | Brekke |
| 5,571,151 A | 11/1996 | Gregory |
| 5,573,531 A | 11/1996 | Gregory |
| 5,606,868 A | 3/1997 | Calvert |
| 5,607,419 A | 3/1997 | Amplatz et al. |
| 5,623,940 A | 4/1997 | Daikuzono |
| 5,643,251 A | 7/1997 | Hillsman et al. |
| 5,649,923 A | 7/1997 | Gregory et al. |
| 5,722,972 A | 3/1998 | Power et al. |
| 5,769,843 A | 6/1998 | Abela et al. |
| 5,817,144 A | 10/1998 | Gregory |
| 5,824,026 A | 10/1998 | Diaz |
| 5,836,513 A | 11/1998 | Smith et al. |
| 5,836,946 A | 11/1998 | Diaz et al. |
| RE36,104 E | 2/1999 | Solar |
| 5,865,801 A | 2/1999 | Houser |
| 5,956,964 A | 9/1999 | Wright |
| 5,961,044 A | 10/1999 | Dalbec et al. |
| 5,968,036 A | 10/1999 | Goodman et al. |
| 5,976,124 A | 11/1999 | Reiser |
| 5,989,243 A | 11/1999 | Goldenberg |
| 5,989,700 A | 11/1999 | Krivopal |
| 5,993,443 A | 11/1999 | Murphy-Chutorian et al. |
| 6,017,188 A | 1/2000 | Benton |
| 6,022,342 A | 2/2000 | Mukherjee |
| 6,039,726 A | 3/2000 | Lewis et al. |
| 6,066,130 A | 5/2000 | Gregory et al. |
| 6,086,053 A | 7/2000 | Natschke et al. |
| 6,117,128 A | 9/2000 | Gregory |
| 6,156,029 A | 12/2000 | Mueller |
| 6,163,641 A | 12/2000 | Eastgate |
| 6,182,463 B1 | 2/2001 | Strussion et al. |
| 6,212,897 B1 | 4/2001 | Wang |
| 6,237,896 B1 | 5/2001 | Hicks et al. |
| 6,271,621 B1 | 8/2001 | Ito et al. |
| 6,290,668 B1 | 9/2001 | Gregory et al. |
| 6,325,362 B1 | 12/2001 | Massey et al. |
| 6,458,098 B1 | 10/2002 | Kanesaka |
| 6,491,647 B1 | 12/2002 | Bridger et al. |
| 6,503,063 B1 | 1/2003 | Brunsell |
| 6,551,302 B1 | 4/2003 | Rosinko et al. |
| 6,691,926 B1 | 2/2004 | Moen |
| 6,742,718 B2 | 6/2004 | Doebler et al. |
| 6,743,208 B1 | 6/2004 | Coyle |
| 6,763,722 B2 | 7/2004 | Fjield et al. |
| 6,789,787 B2 | 9/2004 | Stutts |
| 6,886,411 B2 | 5/2005 | Kjellman et al. |
| 6,963,688 B2 | 11/2005 | Nath |
| 6,974,422 B1 | 12/2005 | Millar |
| 6,994,695 B1 | 2/2006 | Millar |
| 7,021,894 B2 | 4/2006 | Lopatinsky et al. |
| 7,395,676 B2 | 7/2008 | White |
| 7,547,364 B2 | 6/2009 | Polak |
| 8,631,665 B1 | 1/2014 | DeClementi |
| 8,979,828 B2 | 3/2015 | Fix |
| 8,985,557 B2 | 3/2015 | Canipe et al. |
| 9,066,742 B2 | 6/2015 | Splinter |
| 2001/0003790 A1 | 6/2001 | Ben-Haim et al. |
| 2001/0034501 A1 | 10/2001 | Tom |
| 2002/0026188 A1* | 2/2002 | Balbierz ............ A61B 18/1206 606/41 |
| 2002/0068885 A1 | 6/2002 | Harhen et al. |
| 2002/0072647 A1 | 6/2002 | Schock et al. |
| 2003/0051733 A1 | 3/2003 | Kotmel et al. |
| 2003/0216685 A1 | 11/2003 | Porter |
| 2004/0060362 A1 | 4/2004 | Kjellmann et al. |
| 2004/0131299 A1* | 7/2004 | Adoram ............... A61B 8/0833 385/12 |
| 2004/0199156 A1 | 10/2004 | Rioux et al. |
| 2005/0109040 A1 | 5/2005 | Hansen |
| 2005/0131289 A1 | 6/2005 | Aharoni et al. |
| 2005/0148884 A1* | 7/2005 | Parks ..................... A61B 5/037 600/488 |

(56) References Cited

U.S. PATENT DOCUMENTS

| | | | |
|---|---|---|---|
| 2005/0192637 A1 | 9/2005 | Girouard et al. | |
| 2005/0251116 A1 | 11/2005 | Steinke et al. | |
| 2006/0013533 A1 | 1/2006 | Slatkine | |
| 2006/0032259 A1 | 2/2006 | White | |
| 2006/0079813 A1 | 4/2006 | Schlumpf | |
| 2006/0235314 A1 | 10/2006 | Migliuolo et al. | |
| 2007/0119187 A1 | 5/2007 | Kitchens et al. | |
| 2007/0233185 A1 | 10/2007 | Anderson et al. | |
| 2008/0161794 A1 | 7/2008 | Wang et al. | |
| 2008/0234567 A1* | 9/2008 | Tearney | A61B 5/0059 600/407 |
| 2008/0300662 A1 | 12/2008 | Taylor | |
| 2009/0227851 A1* | 9/2009 | Radojicic | A61B 5/032 600/309 |
| 2010/0016842 A1 | 1/2010 | Fix | |
| 2010/0226753 A1 | 9/2010 | Dyson et al. | |
| 2012/0271385 A1* | 10/2012 | Li | C22C 14/00 607/116 |
| 2015/0148790 A1 | 5/2015 | Fix | |
| 2015/0245796 A1 | 9/2015 | Splinter | |

OTHER PUBLICATIONS

Brochure for "Mist & Cool" a Cooling System and Environmental Quality control system, 2001 (with English translation), 6 pages.

European Search Report issued in EP Application No. 12815179.2, dated Apr. 28, 2015, 6 pages.

Grundfest, Warren S., MD, et al., "Laser Ablation of Human Atherosclerotic Plaque Without Adjacent Tissue Injury," JACC vol. 5, No. 4, (Apr. 1985), pp. 929-933.

HRSM Product Catalog 1998-1999, 1 page.

HRSM Product Catalog 2007, 2 Pages.

International Search Report and Written Opinion issued in PCT/US2008/082732 dated Dec. 29, 2008, 6 pages.

International Search Report and Written Opinion issued in PCT/US2012/047543, dated Oct. 5, 2012, 12 pages.

Jaybird Product Catalog Cover 1998-1999, Jaybird Manufacturing, Inc, http://www.jaybird-mfg.com, 2 Pages, Internet Archive Wayback Machine, Apr. 21, 1999.

Jaybird Product Catalog Cover 2007, Jaybird Manufacturing, Inc, http://www.jaybird-mfg.com, 3 pages, Internet Archive Wayback Machine, Apr. 21, 1999.

Merit Medical Systems, Inc. Merit Marquis Flow Switch: Traditional Premarket Notification 510(k). Section 510(k) summary, Jul. 1, 2011, 6 pages.

MeritMedical Flow Control Switch—Instructions for Use. Merit Medical Systems, Inc. 2 pages.

MeritMedical: Flow Control Switch Confidently Control Fluid Flow. Merit Medical Systems, Inc. 2 pages.

NAMIC® Fluid Management: Constructed for Confidence. Configured for Care. Systems for Cardiac Catheterization Labs. Navilyst Medical, Inc. 2009, 11 pages.

Office Action for U.S. Appl. No. 12/061,430 dated Dec. 19, 2018, 10 pages.

Office Action for U.S. Appl. No. 12/176,886 dated Jan. 25, 2013, 10 pages.

Office Action for U.S. Appl. No. 12/176,886 dated Sep. 26, 2012, 12 pages.

Product Catalogue: Peripheral Interventions Vascular Surgery, Boston Scientific, 147 pages.

Qosina Part No. 97337 (Inline Flow Control Switch). Dec. 1, 2012, 1 page.

U.S. Appl. No. 12/254,254, filed Oct. 20, 2008 entitled Liquid Light-Guide Catheter With Optically Diverging Tip.

U.S. Appl. No. 12/061,430, filed Apr. 2, 2018 entitled Laser With Tapered Waveguide.

Design U.S. Appl. No. 29/518,517, filed Feb. 24, 2015.

Design U.S. Appl. No. 29/523,199, filed Apr. 7, 2015.

* cited by examiner

INTRA-VASCULAR DEVICE WITH PRESSURE DETECTION CAPABILITIES USING PRESSURE SENSITIVE MATERIAL

CROSS REFERENCE TO RELATED APPLICATIONS

This application is a divisional U.S. patent application Ser. No. 14/714,925, now U.S. patent Ser. No. 9,289,173, filed May 18, 2015, and titled "Intra-Vascular Device With Pressure Detection Capabilities Using Pressure Sensitive Material", which is a divisional of U.S. patent application Ser. No. 11/937,583, now U.S. Pat. No. 9,066,742, filed Nov. 9, 2007 and entitled "Intra-Vascular Device With Pressure Detection Capabilities Using Pressure Sensitive Material." The entire contents of the above documents are incorporated herein by reference for all purposes.

BACKGROUND

This disclosure relates in general to laser atherectomy and, but not by way of limitation, to laser catheters with pressure sensors among other things.

Atherectomy is a surgical procedure that removes plaque buildup from the lining of an artery using a cutting, rotating or laser catheter. Laser atherectomy may increase the vapor pressure within the fluids or tissues inside an artery during ablation. In some applications, increases in the magnitude and/or frequency of the pressure within a vessel may be a cause for concern. Accordingly, there is a general need in the art for pressure monitoring within a vessel during atherectomy.

BRIEF SUMMARY

Pressure related vascular damage is a potential cause for concern during laser assisted atherectomy. For example, pressure may result from the absorption of laser energy in the medium directly in front of the catheter. The medium can be liquid and/or solid. The absorbed energy may convert the medium from a liquid and/or solid into a gaseous state, which expands and raises the local pressure profile. An alternative mechanism for tissue displacement may be the result of laser-induced plasma formation, yielding an expanding and collapsing molecular plasma with resulting shock waves. The light delivery can be provided, for example, by fiber-optic and/or liquid light-guide delivery to the point at the tip of the catheter. The magnitude and/or gradient in the time development of the pressure wave during ablation may cause stress and strain leading to vascular wall damage. Documented dissection during laser assisted atherectomy may require continuous monitoring of the intra-vascular pressure profile in both time and space during laser ablation procedures to avoid such concerns.

In one embodiment, the present disclosure provides for a laser catheter that includes a pressure sensor that measures the radial pressure response from a laser catheter. Various embodiments may include a piezoelectric pressure sensor. The pressure sensor may include piezoelectric material, for example, a tube, sheet or extrusion of Polyvinylidene Difluoride (PVDF). Sheets of PVDF may be tightly wrapped around the distal tip of a laser catheter. The radial pressure sensor may measure the magnitude and/or the frequency response of the pressure within a vessel, such as, for example, the magnitude and/or frequency of the acoustic pressure waves.

In one embodiment, the present disclosure provides for a laser catheter that includes a pressure sensor that measures the longitudinal pressure response from a laser catheter. A longitudinal pressure sensor may include a band or ring of material that slides over the distal tip of the laser catheter. The band may be secured with the distal tip of the laser catheter using strain sensitive material, such as, for example, PVDF. When the band encounters longitudinal pressure at the distal tip of the laser catheter, the band may move longitudinally along the distal tip of the catheter. As the band moves, the strain sensitive material may register an electric potential proportional to the induced pressure in response to the strain. The longitudinal pressure sensor may measure the magnitude and/or the frequency response of the pressure within a vessel, such as, for example, the magnitude and/or frequency of acoustic pressure waves. The longitudinal pressure sensor may also measure compression in the radial direction. Radial compression can be separated out using signal processing techniques, for example, by applying time gated measurement and/or amplitude separation. In general, longitudinal stretch may yield higher signal strength than compression normal to the strain sensitive material surface. According to another embodiment of the invention, the inner lumen may be coated and attached to a band to measure longitudinal strain in a similar fashion.

The present disclosure also provides for a laser catheter that includes a pressure sensor that measures the longitudinal pressure response of ablation from a laser catheter according to another embodiment of the invention. According to this embodiment, the longitudinal pressure sensor may consist of pressure sensitive filler material, for example PVDF, placed between the fibers (e.g., see pressure sensor 910 of FIG. 9). The pressure sensitive filler material may be covered, for example, by metallic plating that may serve as an electrode and/or provide ablation durability. As the pressure front reaches the distal tip of the catheter the pressure sensitive filler may be compressed and register an electric potential from each individual compartment between the fiber as individual strain sensors or as groupings with the entire fiber packing area acting as one unit in one configuration. Accordingly, the pressure may be measured in both the longitudinal and the radial directions.

In yet another embodiment, the present disclosure provides for methods for using pressure data to determine vessel dimensions and/or tissue type. Other embodiments of the invention may use the pressure measurements to monitor and/or provide a range of suggested operation settings for the physician to select from or automatically adjust operating parameters of the laser. For example, if the pressure within the vessel surpasses a maximum allowable pressure, the laser may cease or reduce energy operation until the pressure stabilizes.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

In the appended figures, similar components and/or features may have the same reference label. Where the reference label is used in the specification, the description is applicable to any one of the similar components having the same reference label.

DETAILED DESCRIPTION OF THE INVENTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It being understood that various changes may be made in the function and arrangement of elements without departing from the spirit and scope as set forth in the appended claims.

In one embodiment, the present disclosure provides for laser catheters with pressure sensors for detecting changes in hemodynamic vascular pressure and/or vascular ablation pressure. Vascular wall damage may result from pressure generation during laser ablation. Monitoring the pressure profile within the vessel may allow a warning mechanism to be activated based on the pressure profile. Embodiments of the invention provide for both longitudinal and radial pressure detection. These embodiments of the invention may continuously monitor the magnitude of the pressure change and/or the frequency response of a pressure wave within a vessel. Various strain sensitive materials may be used to monitor the pressure within a vessel. These pressure measurements may also be used to identify the tissue makeup of the vessel and/or blockage material within the vessel. The pressure measurements may also be used to determine vascular dimensions.

Figure 1:
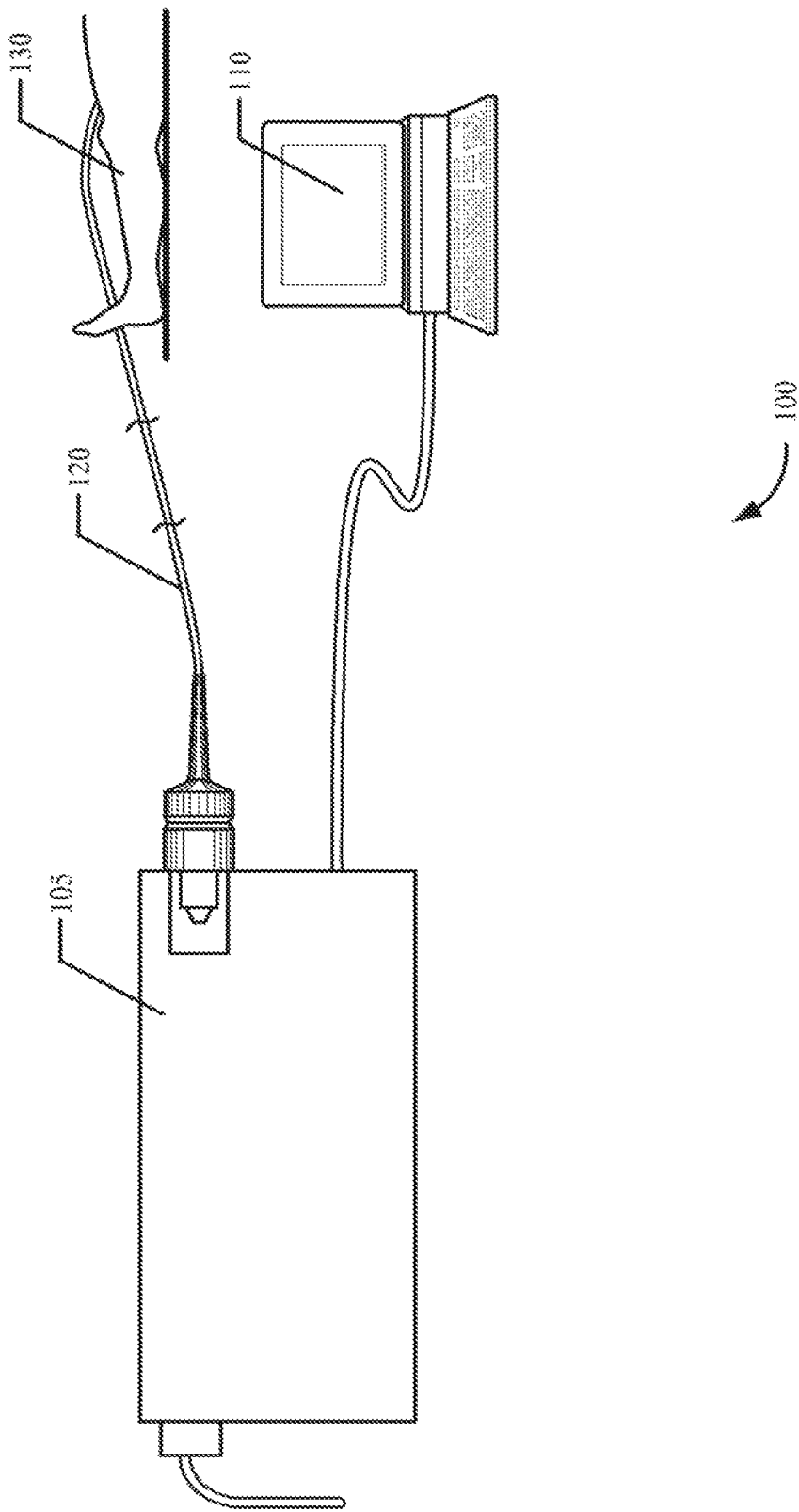
FIG. 1 shows a laser catheter system according to one embodiment of the invention.

FIG. 1 shows a laser system 100 according to one embodiment of the invention. A laser 105 is shown coupled with a user interface 110. In this embodiment the user interface 110 is computer programmed to control the laser 105. The laser 105 and the user interface, in other embodiments of the invention, may be coupled into one system. The laser 105 is connected with a laser catheter 120 that may be inserted into a vessel with a human body 130. The laser catheter 120 is an elongated tube that may include a number of elements. The laser catheter 120 may be of any suitable length A, with a length A between about 350 cm and about 390 cm preferred in some embodiments.

Figure 2:
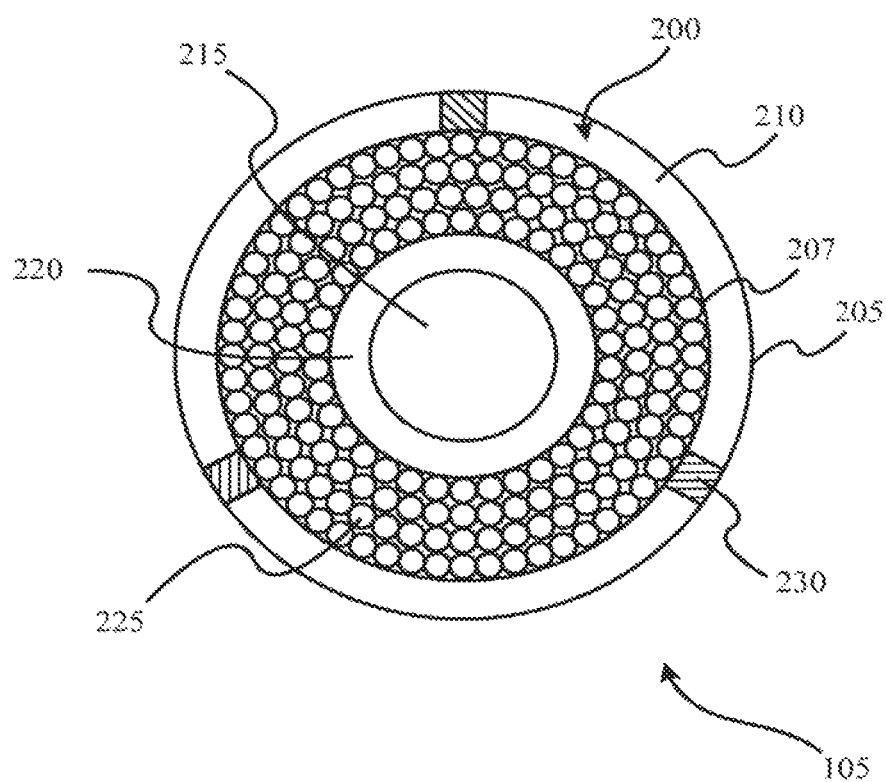
FIG. 2 shows a cross section of a laser catheter according to one embodiment of the invention.

FIG. 2 shows a cross section of the distal tip laser catheter 120 with a radial pressure sensor according to one embodiment of the invention. The laser catheter 120 includes an outer surface 200. The outer surface 200 may enclose the interior of the laser catheter 120. The outer surface, according to this embodiment of the invention, may include an outer electrode 205 and inner electrode 207 and a strain sensitive layer 210. The electrode can be a thin metallic layer which is vapor deposited or mechanically or chemically coated onto the strain sensitive material, or a single wire tip. The strain sensitive layer 210 may include layers of a thin sheet of strain sensitive material. The strain sensitive layer 210, for example, may include polymers of vinylidene fluoride (VDF) such as Polyvinylidene Difluoride (PVDF) or a piezoelectric material. The laser catheter 120 also includes an inner lumen 215, an inner lining 220 and a plurality of fiber optics within a fiber optic core 225, or a liquid that can conduct light while confined by low index-of-refraction tubing material. In some embodiments the outer surface 200 is a continuous piece of material wrapped around the exterior of the laser catheter.

In another embodiment portions of the outer surface 200 are segmented by an acoustic and/or electric separator 230. In such an embodiment, the pressure sensors are segmented and can provide spatial resolution of the measured pressure distribution. Each such segment may provide independent pressure detection and measurement. Multiple conductors may be used for each of the segmented pressure sensing regions. In one embodiment the pressure sensor is segmented into 2, 3, 4, 5, 6, 7, 8 or more segments. The number of segments may depend on the sensitivity of the strain sensitive materials and/or the signal output strength. Without the segments, in some embodiments of the invention, the sensor yields a single average pressure around the entire distal tip of the laser catheter.

In some embodiments of the invention, the strain sensitive layer 210 responds to changes in the pressure of the vessel. The inner electrode 207 and the outer electrode 205 provide an electrical response from the strain sensitive layer 210 that may be communicated back to the laser system 105. A wire may replace one or more of the fiber optics. The wire may be electrically connected with the inner and/or outer electrodes 205, 207 and the laser system 105. In another embodiment of the invention, a light source, such as an LED, may be coupled with the pressure sensor. The light source may convert the electrical pressure signal to an optical pressure signal that may be transmitted through a fiber optic. The optical pressure signal may include a frequency or magnitude. This configuration provides a radial pressure sensor that detects changes in pressure radially from the laser catheter.

The inner lining 220 of the laser catheter 105 may include a one or more layers of strain sensitive material according to one embodiment of the invention. Moreover, the lumen may also include a piezoelectric material that responds electrically to pressure changes according to one embodiment of the invention.

In the embodiment shown in FIG. 2, the strain sensitive layer 210 responds electrically to changes in the pressure incident coaxially on the outer surface of the laser catheter. Such a configuration may, for example, allow the strain sensitive layer to respond to the frequency response of the vessel when the laser catheter is pulsing. Additionally the longitudinal pressure sensor can respond to advancement pressure created by the frictional or normal force from the medium the catheter is passed through. The mechanical pressure resulting from the push force on the catheter can provide suggestions regarding the advancement rate and the push force with respect to the compliance of the tissue ahead of the catheter. A user may note the advancement pressure and adjust advancement of the laser catheter accordingly.

Figure 3:
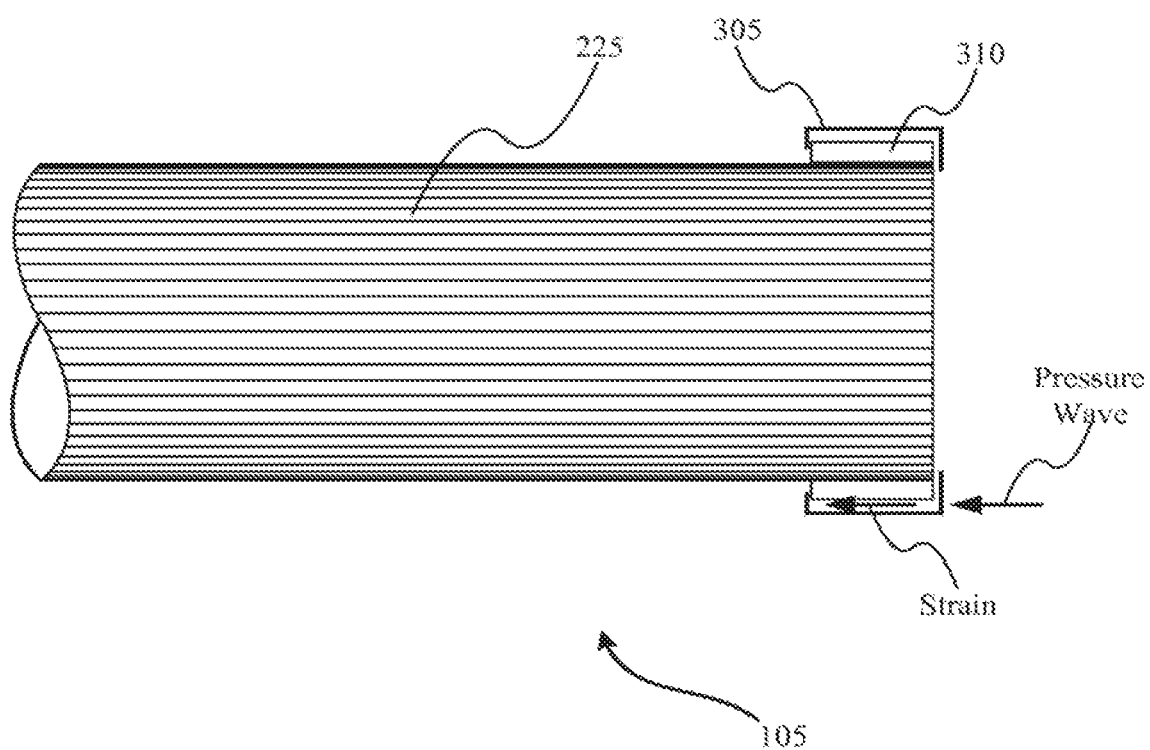
FIG. 3 shows a cross sectional side view of a laser catheter according to one embodiment of the invention.

FIG. 3 shows a cross sectional side-view of a longitudinal pressure sensor at the distal tip of a laser catheter according to another embodiment of the invention. A plurality of fiber optics are shown within a fiber core 225 that run the length of the laser catheter. The distal tip of the laser catheter includes a band 305 that wraps around the exterior of the laser catheter 105. The band 305 may be comprised of any biocompatible metal, for example, Platinum. The band 305 can simultaneously serve as an electrode as well. The band is coupled to the distal tip of the laser catheter 120 with strain sensitive material 310, for example, PVDF. Any other type of strain sensitive material may also be used. If a pressure wave approaches the distal tip of the laser catheter 120 along a longitudinal path as shown, the configuration of the sensor will detect this longitudinal displacement and/or pressure wave. Pressure waves may move the band 305 relative to the tip of the laser catheter 120 causing strain within the strain sensitive material 310. In response to the pressure on the band 305 and the corresponding strain in the strain sensitive material 310, an electrical potential may be generated in the strain sensitive material 310 and communicated to controller or laser through the catheter. The magnitude and frequency of the pressure may be measured. The longitudinal pressure sensor with Platinum band may be segmented to provide spatial resolution.

Figure 4:
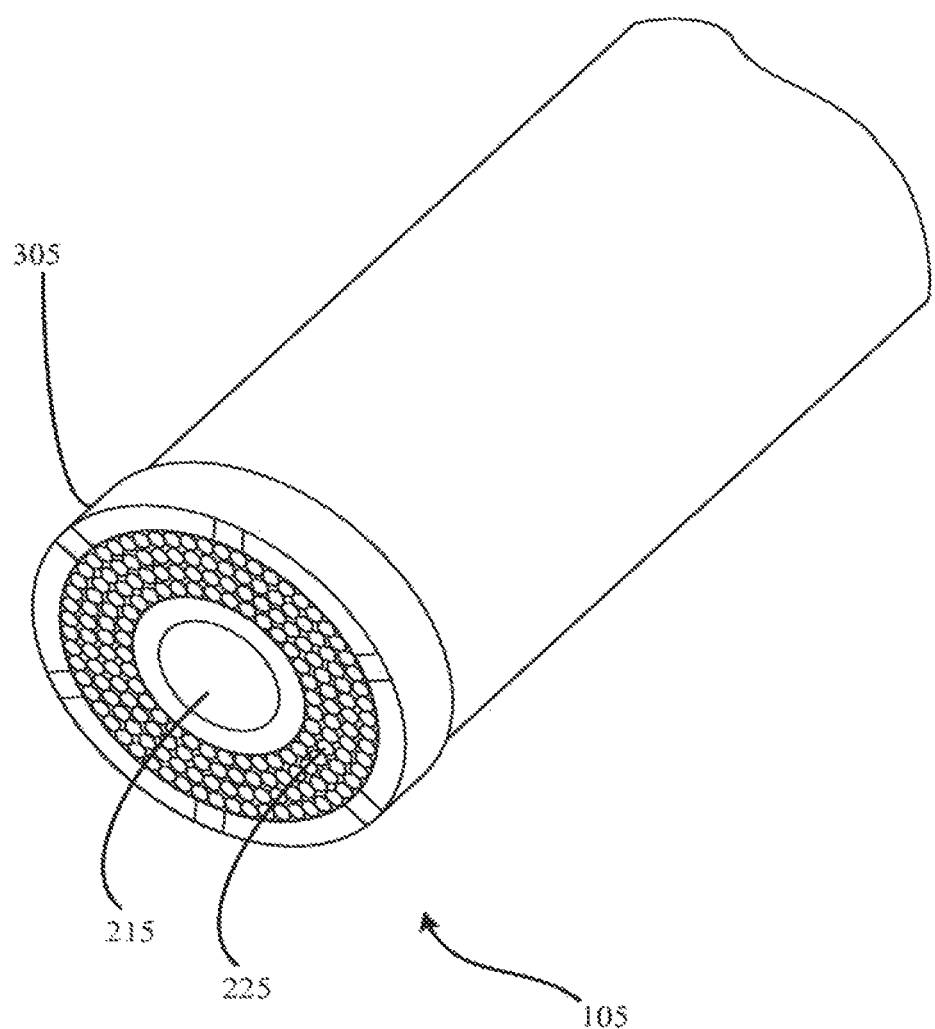
FIG. 4 shows a perspective view of a laser catheter according to one embodiment of the invention.

FIG. 4 shows a perspective view of a laser catheter 120 according to one embodiment of the invention. A band 305 is shown that is coupled with the distal tip of the laser catheter with strain sensitive material and acts as a longitudinal pressure sensor is shown. In another embodiment, the laser catheter 120 may include both a longitudinal pressure sensor as depicted in FIG. 3 as well as the radial pressure sensor shown in FIG. 2.

Figure 5:
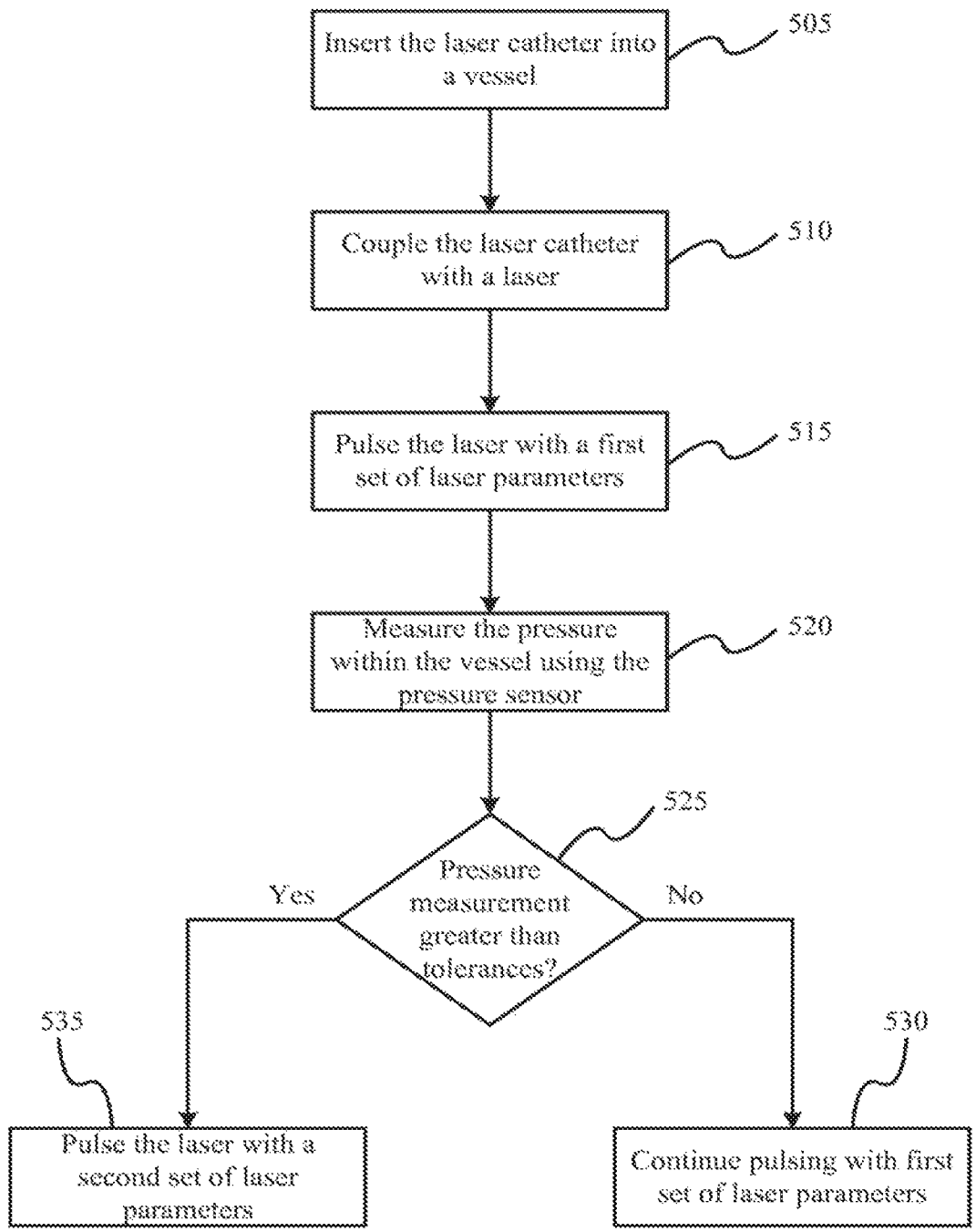
FIG. 5 shows a flowchart depicting a method for adjusting laser catheter pulsing parameters in response to the measured pressure within a vessel according to one embodiment of the invention.

FIG. 5 shows a flowchart depicting a method for adjusting laser catheter pulsing parameters in response to the measured pressure within a vessel according to one embodiment of the invention. A laser catheter is inserted into a vessel at block 505. For example, the vessel may be an artery, vein, urethra, fallopian tube, connecting junction between brain ventricles or the like. The laser catheter may then be coupled with a laser at block 510. The inserting of the laser catheter and the coupling of the laser catheter with a laser may be performed by a user, for example, a technician, nurse and/or doctor.

For example, the repetition rate may be set at about 80 Hz and the fluence at 60 mJ/mm$^2$. The repetition rate may vary between 10 Hz and 160 Hz according to one embodiment of the invention. In another embodiment of the invention, the repetition rate is between 40 Hz and 80 Hz. In another embodiment of the invention, the fluence is set below 100 mJ/mm$^2$. In another embodiment, the fluence is set below 120 mJ/mm$^2$. The laser may then be pulsed with a first set of laser parameters at block 515. In some embodiments, energy density settings may go as high as 200 mJ/mm$^2$, and the repetition rate may be as high as the kHz or MHz ranges. For example, the fluence and/or the repetition rate may be set to operate with default parameters. These default parameters may be input by the user. These default parameters may also be dependent on the type of catheter, or various patient conditions.

While the laser is pulsing with the first set of laser parameters, the pressure within the vessel near the distal tip of the laser catheter may be monitored and/or measured at block 520. The frequency response and/or the magnitude of the pressure may be measured in one embodiment. The longitudinal pressure and/or the radial pressure may be measured in another embodiment. At block 525, it is determined whether the pressure magnitude or frequency response reaches above a pressure tolerance. These tolerances may be dependent on the type of catheter, various patient characteristics, preset by the user and/or be a default within the system. If the pressure is above tolerance, the laser is pulsed with a second set of laser parameters at block 525. Alternatively, a suggestion for a new set of operating parameters may be presented to the user though a user interface. In one embodiment of the invention, if the measurements are well above tolerance, the fluence is set to zero. In another embodiment of the invention, the second set of laser parameters may include lower fluence and/or a lower repetition rate that may or may not depend on the measured pressure.

Figure 6:
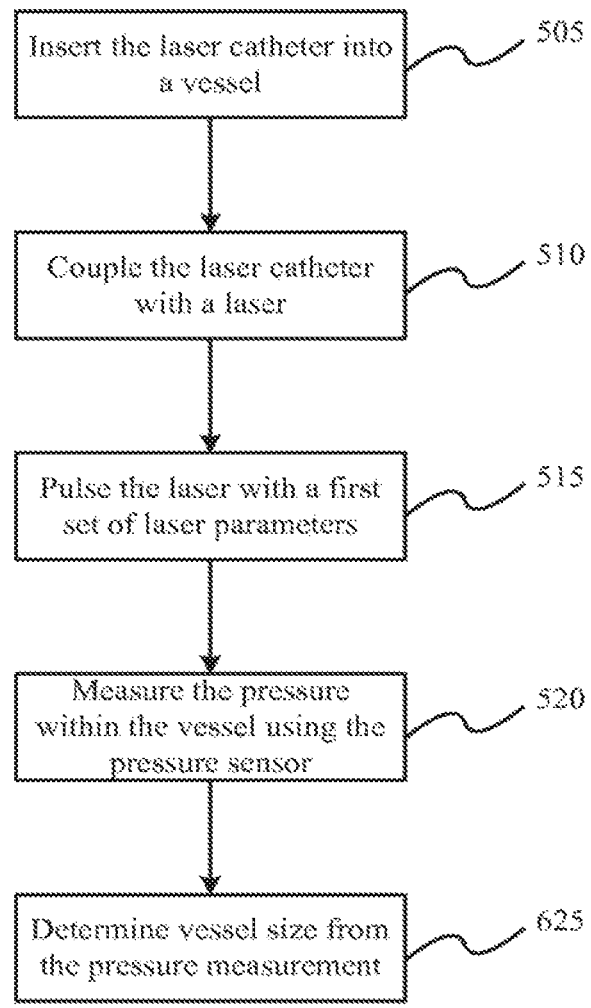
FIG. 6 shows a flowchart depicting a method for using a laser catheter to determine the size of a vessel in response to the measured pressure within the vessel according to one embodiment of the invention.

FIG. 6 shows a flowchart depicting a method for using a laser catheter to determine the size of a vessel, or the lumen inside the occlusion in response to the measured pressure within the vessel according to one embodiment of the invention. Blocks 505, 510, 515, 520 are the same as the blocks shown in FIG. 5. The pressure measurements within the vessel may then be used to determine the type of tissue the vessel is made of or the type of material within the vessel. The absorption of the laser energy may result in a shock-wave that has a frequency spectrum signature corresponding to Young's modulus of the medium. Young's modulus is defined as the ratio of stress to strain on the extension plane along the direction in which the force acts. For example, the pressure bubble expansion within a vessel is the driving force on the stress and strain components. For instance, Calcium and fat will have very different values for the Young's modulus and thus particular resonance frequencies. Other types of material may return resonance frequencies that depend on the material type.

Additional signal processing using returned spatially distributed pressure measurements may provide Poisson's ratio for various tissue conditions. The Poisson ratio is defined as the transverse strain (normal to the applied force) divided by the relative extension strain, or axial strain (in the direction of the applied force), and requires a dimensional analysis of the pressure wave pattern. Poisson's ratio is a direct indication of specific tissue compliance factors. Poisson's ratio may also provide a supplementary tool to accurately identify tissues at respective pressure frequency patterns.

Figure 7:
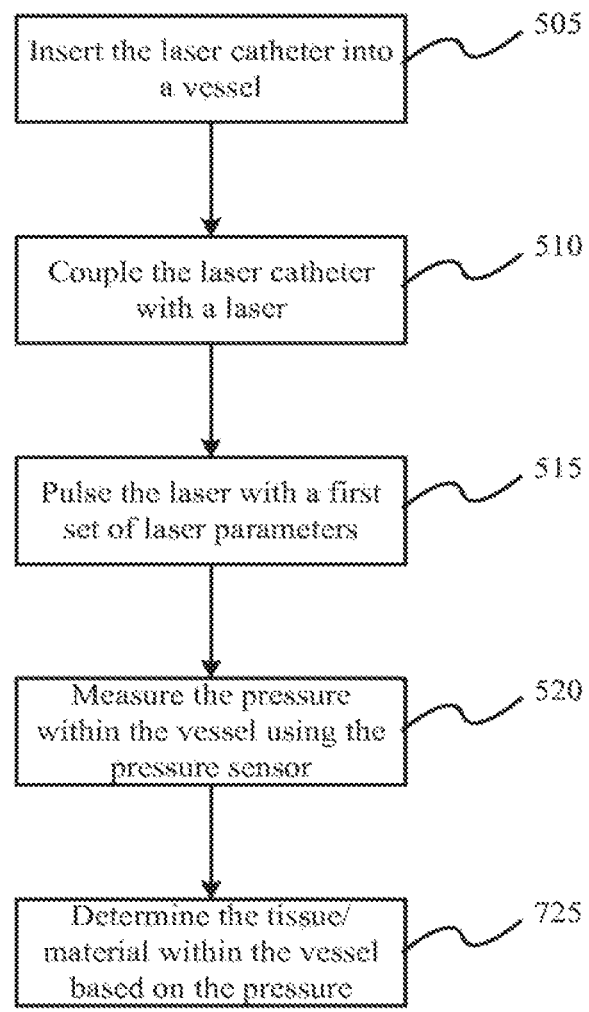
FIG. 7 shows a flowchart depicting a method for using a laser catheter to determine the tissue or material type of a vessel in response to the measured pressure within the vessel according to one embodiment of the invention.

FIG. 7 shows a flowchart depicting a method for using a laser catheter to determine the tissue or material type of a vessel in response to the measured pressure within the vessel according to one embodiment of the invention. Blocks 505, 510, 515, 520 are the same as the blocks shown in FIG. 5. The pressure measurements within the vessel may be used to determine vessel dimensions. Vessel dimensions may be a function of the resonance frequency of sound waves created by the laser catheter when pulsing. The frequency of the sound wave may be measured by the pressure sensor.

The resonance frequency ν of the sound wave created by the local heating and subsequent expansion, depends on the value of Young's modulus of the tissue and the local dimensions. For example, the resonance frequency: ν of the material excited by the laser pulse can be written for an arbitrary tissue geometry as shown in equation 1:

$$\upsilon = C\sqrt{\frac{E}{\rho}}\frac{d}{w*h} \qquad \text{eq. 1}$$

where d represents the depth of the medium, w the width, h the height of the structure of the medium respectively and ρ the density of the material. E is Young's Modulus of the tissue. In general, the dimensional analysis correlates to the Moment of Inertia of the geometry of the medium under irradiation. The constant C denotes a parameter that depends on the geometric nature of the particular medium (which may be related to the moment of inertia of the structure and the absorption depth of the laser beam). Accordingly, if the resonance frequency is known, using Young's Modulus and density a rough dimensionality may be determined. For example, signal processing, including Fourier spectral analysis can be used to separate the influences of different tissue dimensions and alternative tissue compositions.

Eq. 1 may be rewritten in another form, that may be convenient for some applications.

$$v = A\sqrt{\frac{E}{\rho L^2}} \quad \text{eq. 2}$$

where A is a constant that depends on the mode of excitation and L represents the representative dimension of the system geometry. Using either eq. 1 or eq. 2, one may determine the size of the vessel or area being irradiated by the laser catheter. Additional theoretical descriptions may be derived or have been published to outline the phenomenon of frequency dependence on geometry and composition, alternative techniques may be used to derive the tissue parameters.

Figure 8:
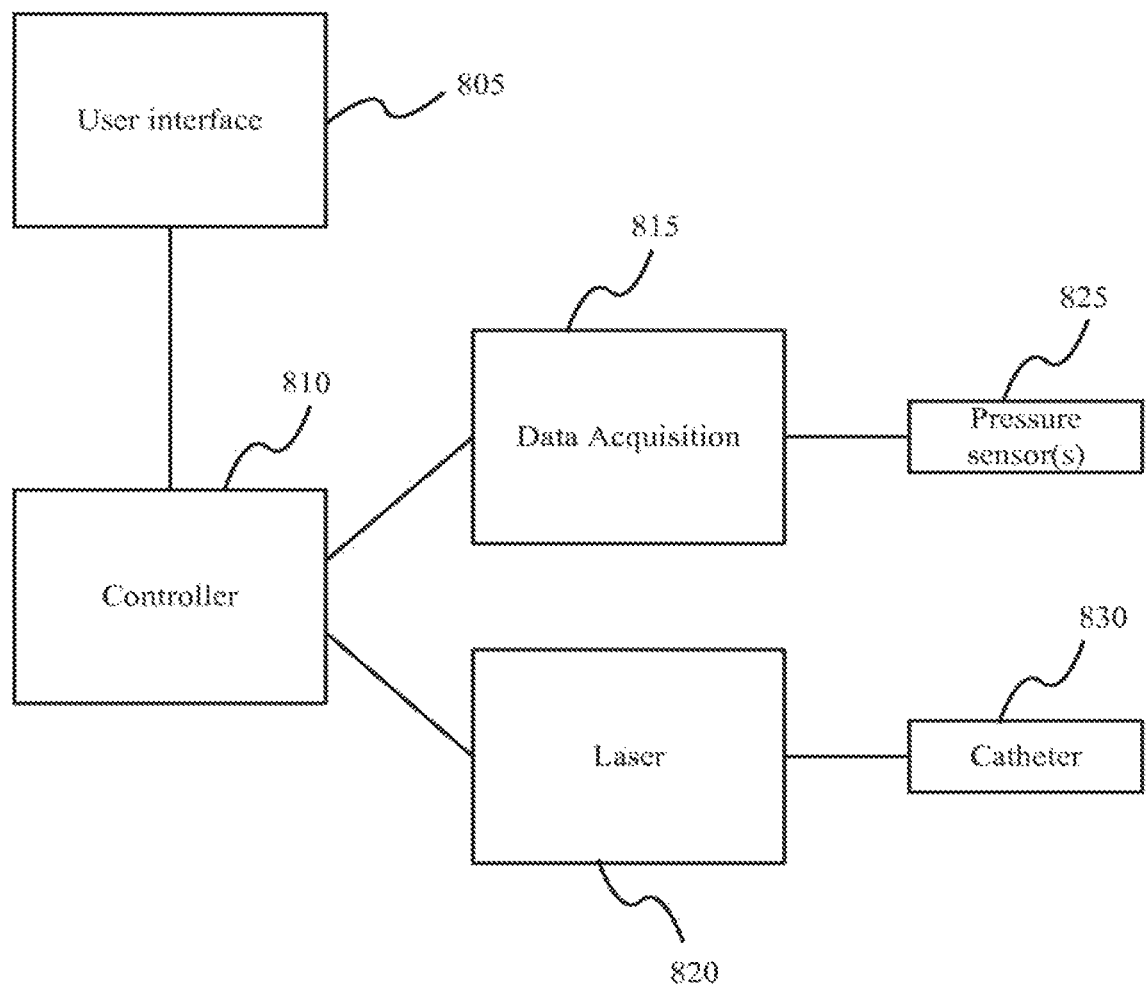
FIG. 8 shows a functional block diagram of various components that may be used according to embodiments of the invention.
Figure 9:
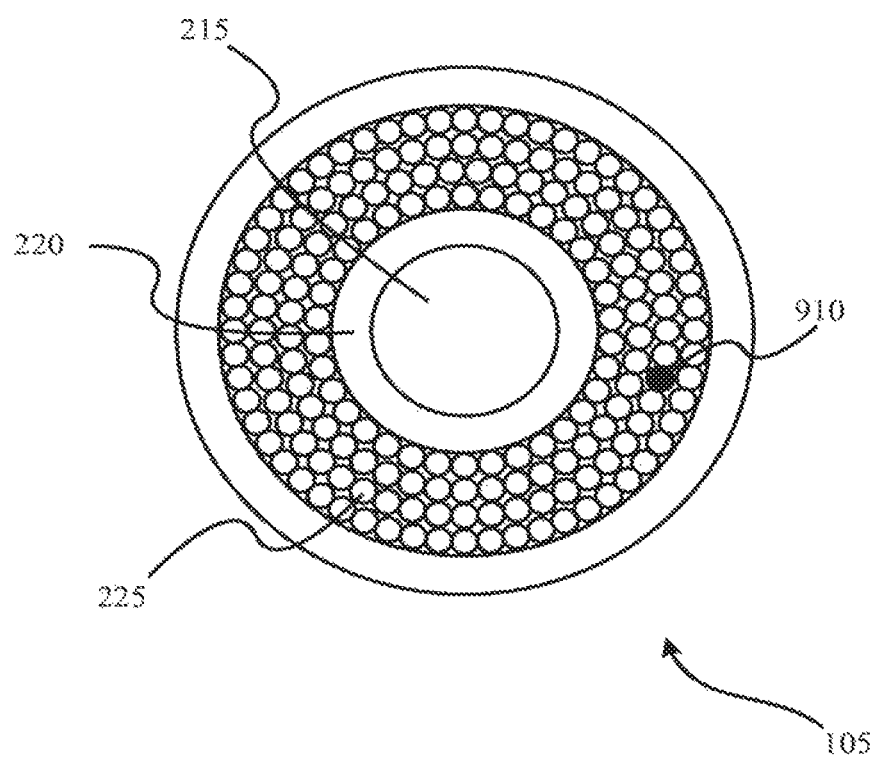
FIG. 9 shows a cross section of a laser catheter according to one embodiment of the invention.

FIG. 8 shows a functional block diagram of various components that may be used according to embodiments of the invention. A controller 810 is coupled with a user interface 805, data acquisition unit 815 and a laser 820. These four components may be incorporated within a single operating unit or product. The four components may also be independent. The user interface 805 may include a computer, a screen, touchpad, touch screen, mouse, keyboard, etc. for user input and output. The controller 810 may include a computer system or any type of micro controller with programming code and/or software for controlling the various components.

The controller 810 provides operating parameters to the laser 820, such as the operating fluence and/or the repetition rate. The laser 820 is coupled with the laser catheter 830 and may be used in vessel ablation. The pressure sensor 825 may be coupled with the distal tip of the laser catheter 830. The pressure sensor 825 may detect the pressure within the vessel near the distal tip of the laser catheter. The pressure sensor 825 may transduce pressure into an electric potential that is acquired at the data acquisition unit 815. The data acquisition unit 815 may perform signal processing on the received signals and/or may buffer the received signals. The data acquisition unit 815 may also translate the electric potential into relative and/or absolute pressure or the frequency profile of the pressure changes over time. This information may then be transmitted to the controller 810.

The controller may use the pressure information in a number of different ways. For example, the controller may determine vessel dimensions and/or determine the type of tissue within the vessel using the pressure data. The controller may report the data to a user through the user interface. The controller may limit the fluence and/or repetition rate of the laser in response to the pressure data.

Various embodiments of the invention use strain sensitive materials at the distal tip of a laser catheter to produce an electric potential proportional to the induced strain. These strain sensitive materials may be polymer macromolecular structures that produce an electrical signal as a result of deformation of the polymer layer. One example of a piezoelectric polymer is a material that can be produced in the form of tube, sheet or film, for example, materials with polymers of vinylidene fluoride (VDF) as principle components. Strain sensitive piezoelectric materials may be applied on the distal tip of a laser catheter by solution deposition technique as well as extrusion techniques. Additional methods for piezo-electric sensor manufacturing include machining. Other techniques may include procuring sheets of the piezoelectric material and wrapping the distal tip of the laser catheter with one or more layers. Each such layer may be 200 microns or less.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored. The signal processing may require a look-up table for tissue and size reference in relation to measured signal patterns (e.g. frequency spectrum, frequency components, amplitude, temporal information, etc.). Advanced signal processing technique may be required to resolve the full detail of all tissue and laser parameter information obtained from the measured signals.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels and/or various other mediums capable of storing, containing or carrying instruction(s) and/or data.

While the principles of the disclosure have been described above in connection with specific apparatuses and methods, it is to be clearly understood that this description is made only by way of example and not as limitation on the scope of the disclosure.

What is claimed is:

1. A method for using a laser catheter, the method comprising:
   inserting the laser catheter within a cavity, wherein the laser catheter includes a fiber optic core, a distal tip and a pressure sensor disposed near the distal tip, wherein the fiber optic core channels laser light from a laser to the distal tip, wherein the pressure sensor comprises a plurality of segments disposed along the laser catheter at a common radial distance from the fiber optic core but at different radial positions around the fiber optic core, wherein the segments are formed of an electrically conductive material, wherein each of the segments is circumferentially separated from the other segments by a separator that is a separate member inserted between the electrically-conductive segments around a diameter of an outer surface of the laser catheter to thereby electrically and acoustically isolate the segments from each other, and wherein each segment of the segments is configured to independently sense pressure applied to that segment;
   pulsing a laser coupled with the laser catheter using a first set of laser parameters; and
   separately measuring the frequency response of the material within the cavity in response to the laser pulsing using each of the plurality of segments of the pressure sensor to thereby determine pressures applied at each of the different radial positions around the fiber optic core while the pressure sensor is disposed within the cavity.

2. The method according to claim 1, further comprising determining the size of the cavity using the measured frequency response.

3. The method according to claim 1, further comprising identifying the tissue within the cavity based on at least the measured frequency response.

4. The method according to claim 1, wherein the pressure sensor comprises an outer electrode and inner electrode and a strain sensitive layer disposed between the outer electrode an inner electrode.

5. The method according to claim 1, wherein measuring the frequency response of the material within the cavity comprises measuring the frequency response using the plurality of segments.

6. The method according to claim 1, wherein the pressures applied at each of the different radial positions around the fiber optic core are measured in the radial direction normal to the fiber optic core.

7. The method according to claim 6, wherein the pressures applied at each of the different radial positions around the fiber optic core are measured in the longitudinal direction parallel to the fiber optic core.

8. The method according to claim 1, wherein the pressure sensor comprises at least two segments and one separator.

9. The method according to claim 8, wherein the frequency response is measured using pressure readings from each of the at least two segments.

10. The method according to claim 1, wherein the pressure sensor comprises at least three segments and two separators.

11. The method according to claim 10, wherein the frequency response is measured using pressure readings from each of the at least three segments.

12. A method for using a laser catheter, the method comprising:
    inserting the laser catheter within a cavity, wherein the laser catheter includes a fiber optic core, a distal tip and a pressure sensor disposed at the distal tip, wherein the fiber optic core channels laser light from a laser to the distal tip, wherein the pressure sensor comprises a plurality of segments disposed at the distal tip, wherein each of the segments is located at a different radial position around the fiber optic core and wherein the segments are circumferentially separated from each other by at least one separator disposed at the distal tip and around a diameter of an outer surface of the laser catheter, wherein the segments are formed of an electrically conductive material and the at least one separator is a separate member inserted between the electrically-conductive segments to thereby electrically and acoustically isolate the segments from each other, and wherein each segment of the segments is configured to independently sense pressure applied to that segment;
    pulsing a laser coupled with the laser catheter using a first set of laser parameters; and
    measuring the frequency response of the material within the cavity in response to the laser pulsing using each of the plurality of segments of the pressure sensor to thereby determine pressures applied at each of the different radial positions around the fiber optic core while the pressure sensor is disposed within the cavity.

13. The method according to claim 12, wherein the pressure sensor comprises at least three segments and two separators.

14. The method according to claim 12 wherein the pressures applied at each of the different radial positions around the fiber optic core are measured in the radial direction normal to the fiber optic core.

15. The method according to claim 12 wherein the pressures applied at each of the different radial positions around the fiber optic core are measured in the longitudinal direction parallel to the fiber optic core.

\* \* \* \* \*